US011877566B2

(12) United States Patent
Fotiadis

(10) Patent No.: US 11,877,566 B2
(45) Date of Patent: Jan. 23, 2024

(54) INSECT LARVAE REARING

(71) Applicant: Entomics Biosystems Limited, Cambridge (GB)

(72) Inventor: Fotis Fotiadis, Cambridge (GB)

(73) Assignee: Entomics Biosystems Limited, Cambridge (GB)

(*) Notice: Subject to any disclaimer, the term of this patent is extended or adjusted under 35 U.S.C. 154(b) by 10 days.

(21) Appl. No.: 16/648,200

(22) PCT Filed: Sep. 13, 2018

(86) PCT No.: PCT/GB2018/052608
§ 371 (c)(1),
(2) Date: Mar. 17, 2020

(87) PCT Pub. No.: WO2019/053439
PCT Pub. Date: Mar. 21, 2019

(65) Prior Publication Data
US 2020/0253176 A1 Aug. 13, 2020

(30) Foreign Application Priority Data

Sep. 18, 2017 (GB) ..................... 1714964
Jul. 23, 2018 (GB) ..................... 1811973

(51) Int. Cl.
*A01K 67/033* (2006.01)
*A23K 50/90* (2016.01)
(Continued)

(52) U.S. Cl.
CPC .............. *A01K 67/033* (2013.01); *A01K 1/00* (2013.01); *A23K 10/26* (2016.05); *A23K 50/90* (2016.05)

(58) Field of Classification Search
CPC ........ A01K 1/00; A01K 67/033; A23K 10/26; A23K 50/90
See application file for complete search history.

(56) References Cited

U.S. PATENT DOCUMENTS 4,262,633 A * 4/1981 Taboga .............. A01K 67/0332
119/6.7
5,759,224 A * 6/1998 Olivier ................... C05F 17/05
71/9
(Continued)

FOREIGN PATENT DOCUMENTS

CA 2979709 A1 * 9/2016 .......... A01K 67/033
CN 101120147 A 2/2008
(Continued)

OTHER PUBLICATIONS

International Search Report and Written Opinion received in Patent Cooperation Treaty Application No. PCT/GB2018/052608, dated Mar. 21, 2019.
(Continued)

*Primary Examiner* — Monica L Perry
*Assistant Examiner* — Aaron M Rodziwicz
(74) *Attorney, Agent, or Firm* — Julia A. Kim; In Vivo Patent Law

(57) ABSTRACT

An insect larvae rearing system is disclosed. The system comprises a waste management module configured to receive organic waste and to convert the organic waste into a feed for insect larvae and at least one rearing module configured to handle a plurality trays for holding or housing larvae and to provide the feed to the trays. The feed is supplied directly from the waste management module to each of the at least one rearing modules.

14 Claims, 9 Drawing Sheets

(51) Int. Cl.
*A23K 10/26* (2016.01)
*A01K 1/00* (2006.01)

(56) References Cited

U.S. PATENT DOCUMENTS

| | | | |
|---|---|---|---|
| 8,931,442 B2 | 1/2015 | Li et al. | |
| 9,302,949 B2* | 4/2016 | Milin | C05F 17/05 |
| 10,159,229 B2* | 12/2018 | Marchant | F21V 7/22 |
| 10,188,084 B2* | 1/2019 | Leo | A23K 20/174 |
| 2011/0139075 A1* | 6/2011 | Shapiro Ilan | A01K 67/033 |
| | | | 119/6.5 |
| 2013/0319334 A1* | 12/2013 | Newton | A01K 29/00 |
| | | | 119/6.5 |
| 2014/0020630 A1* | 1/2014 | Courtright | A01K 67/033 |
| | | | 119/6.6 |
| 2017/0311612 A1* | 11/2017 | Leo | A21D 2/34 |
| 2017/0360014 A1* | 12/2017 | Hall | A01K 5/02 |
| 2018/0007875 A1* | 1/2018 | Hall | A01K 7/02 |
| 2018/0064079 A1* | 3/2018 | Hasa | A01K 67/033 |
| 2019/0191677 A1* | 6/2019 | Massaro | A01K 67/033 |
| 2019/0191678 A1* | 6/2019 | Alrayya | A23K 50/90 |
| 2019/0387704 A1* | 12/2019 | Hall | A01K 67/033 |

FOREIGN PATENT DOCUMENTS

| | | | | | |
|---|---|---|---|---|---|
| CN | 101761359 | A | 6/2010 | | |
| CN | 206043152 | U | 3/2017 | | |
| EP | 2912958 | A1 | 9/2015 | | |
| JP | 2002-011440 | A | 1/2002 | | |
| JP | 2010-110307 | A | 5/2010 | | |
| JP | 2014-083025 | A | 5/2014 | | |
| KR | 20130127696 | A | 11/2013 | | |
| KR | 1020150138992 | A | 12/2015 | | |
| WO | 2006-093757 | A1 | 9/2006 | | |
| WO | WO-2016153339 | A1 * | 9/2016 | ........... | A01K 67/033 |
| WO | WO-2016153340 | A2 * | 9/2016 | ........... | A01K 67/033 |

OTHER PUBLICATIONS

Search and Examination Report received in Great Britain Application No. GB1714964.2, dated Mar. 16, 2018.
EntoCube, "Our Story", https://entocube.com/en/our-story, dated Sep. 1, 2019.
Chinese Office Action (and translation) received in Chinese Application No. 201880060252.X, dated Jul. 2, 2021, 15 pages.
Examination Report received in European Application No. 18792439.4, dated Apr. 3, 2023, 17 pages.

* cited by examiner

INSECT LARVAE REARING

RELATED APPLICATION

This application is a 35 U.S.C. § 371 national phase application of PCT/GB2018/052608, filed Sep. 13, 2018, which claims priority to GB Application No. 1714964.2 filed Sep. 18, 2017 and GB Application No. 1811973.5 filed Jul. 23, 2018. The contents of each are hereby incorporated by reference in their entirety.

FIELD OF THE INVENTION

The present invention relates to insect larvae rearing. In particular, it relates to a system for rearing insect larvae which can be assembled using one or more modules for preparing feed for insect larvae and one or more modules for rearing the insect larvae using the feed.

BACKGROUND

The Food and Agricultural Organization (FAO) of the United Nations estimates that the world will need to produce 70% more food to feed the world's growing population in 2050. Meanwhile, over 1.3 bn tonnes of food waste is produced globally each year which, also produces more than 3GtCo2-equivalent in greenhouse gases.

Attempts have been made over the past decade to utilize different types of technologies to upcycle waste. While waste valorisation of plastics, metals and paper has been widely accepted and adopted, valorisation of organic waste (such as food waste) faces challenges. The volatile and time-sensitive nature of the waste (in other words, the fact that the waste degrades quickly) and the fact that the food waste generates unpleasant odours tends to pose additional problems and health hazards compared with processing of other forms of waste.

Other than composting, one approach to organic waste valorisation is anaerobic digestion. Anaerobic digestion uses microbes to break down organic matter. During this chemical reaction, methane is released, captured and converted into bio-gas used for power generation Even though anaerobic digestion offers a better alternative to landfill, it is capital intensive, due to high plant costs, while the process itself is sensitive to changes in ambient conditions and feedstock composition. Moreover, although anaerobic digestion harnesses valuable trapped nutrients by converting them into electricity, it does not address the issue of food scarcity.

One naturally-occurring way of processing organic waste is to use insect larvae for bioconversion. Unlike anaerobic digestion, which breaks down organic waste into simpler molecules (ultimately generating methane), insect larvae can be used to convert organic waste into more complex hydrocarbons, such as proteins and bio-oils, which are accumulated in the bodies of the larvae. Moreover, insects tend to be comparatively more resilient and adaptable to changes in environment and feedstock.

Research has been directed to industrializing and scaling up waste valorisation through insect bioconversion. However, the approaches taken so far tend to be expensive, complex to manage and difficult to scale. Furthermore, the cost of waste logistics can inhibit waste valorisation.

US 2013/0319334 A1 describes a system for rearing larvae. The system includes a plurality of culture trays arranged in at least one stack of trays, each stack comprising multiple levels of trays, each tray comprising an open-topped basin adapted to receive larvae and larval food, a feed delivery system adapted to automatically deliver larval feed to individually selected culture trays, and a water delivery system adapted to automatically deliver water to the culture trays.

WO 2015/013826 A1 discloses producing insecticidal black soldier fly (*Hermetia illucens*) frass, and using the frass for nutritional and insect pest control activity in soils and/or on foliage.

US 2016/0066552 A1 describes breeding insects using individual crates, wherein at least a portion of each crate is filled with a substrate, containing feed stock, and immature phases of insects.

WO 2016/166471 A1 describes a farm for rearing insects, comprising a zone in which insects being reared are stored in containers using pallet racks.

Reference is also made to Imre-Antalfy: Abstract "Bugs in a Box", 2016 https://www.hsr.ch/uploads/tx_icscrm/2016_DAB-EEU_FINAL_low_ES_15.pdft Reference is also made to https://www.entocube.com/solutions/ which describes a cricket farming system.

SUMMARY

According to a first aspect of the present invention there is provided a system for rearing insect larvae. The system comprises a waste management module configured to receive organic waste (such as food waste) and to convert the organic waste into a feed for insect larvae, or at least one container for a feed for insect larvae, and at least one rearing module configured to handle a plurality of trays for holding or housing the insect larvae and to provide the feed to the trays. The feed, which may be in the form of slurry, is supplied directly from the waste management module or the at least one container to each of the at least one rearing modules.

Thus, by taking a modular approach, the system can be assembled on-site at or close to a source or group of sources of organic waste and can be scaled according to the volume of organic waste generated by the source(s) of waste (which can vary seasonally). This can help to reduce the distance over which organic waste—which can be comprised of up to 80% water content by mass—is transported, thereby greatly reducing logistics costs and associated CO2 emissions. Alternatively, the system can be positioned at a location, such as a poultry farm or other type of animal farm, where live insect larvae can be consumed, for example, by chickens or other livestock. This can help provide a high-quality feed for livestock. This can also help to reduce logistics costs and associated CO2 emissions by not needing to transport larvae.

The waste management module and/or each of the at least one rearing modules comprises a respective transportable container. The transportable container may take the form of a shipping container, such as a nominal 10-foot (3.0 m), 20-foot (6.1 m) or 40-foot (12.2 m) shipping container. Thus, modules can be manufactured in part or whole at one location and delivered on-site which can help to reduce manufacturing costs.

The system may comprise at least one tube, for example in the form of pipe or hose, for supplying the feed from the waste management module to each of the at least one rearing module.

The system may comprise at least two rearing modules, for example, between four and ten rearing modules, or more than ten rearing modules, for example between ten and twenty rearing modules.

More than one rearing system may be installed at one site. In other words, there may be more than one waste management module.

Each of the at least one container may be arranged to supply a respective rearing module.

The system may be located at the same site as or near to (<5 km) an insect larvae consumer installation (which may take the form of an animal farm, such as a poultry farm). The system may be located at different sites from or far from (>5 km) an insect larvae consumer installation. The system may serve more than one insect larvae consumer installations, for example, more than one farm. A plurality of farms may be clustered (for example, within a radius of 5 km). The system may be located at one of the plurality of farms.

According to a second aspect of the present invention there is provided a waste management module for converting organic waste into a feed for insect larvae. The waste management module may comprise a container. The waste management module includes and the container may house, a hopper for receiving organic waste from outside the container via an opening in a container wall or roof, a shredder in communication with the hopper, arranged to receive organic waste and to output shredded organic waste, a de-waterer configured to reduce water content of the shredded organic waste or processed shredded organic waste obtained from the shredded organic waste and to output a feed for insect larvae and a storage vessel (for example another hopper) for the feed.

The waste management module may further comprise at least one pump for delivering the feed from the storage vessel to one or more tubes, for example pipes or hoses, for delivering the insect larvae feed to an insect larva rearing module. The at least one pump may be housed in the container. One pump may be provided for each tube.

The waste management module may further comprise a pasteurizer configured to receive shredded organic waste and to output pasteurized shred organic waste.

The container may take the form of a shipping container, such as a nominal 10-foot (3.0 m), 20-foot (6.1 m) or 40-foot (12.2 m) shipping container.

According to a third aspect of the present invention there is provided a rearing module for rearing insect larvae. The rearing module includes and the container may house, a tray handling system arranged to receive trays, which may interlock to form a stack or which may be inserted in a rack to form a stack, at a loading/unloading point and to move the trays or the rack of stacked trays, and a feed delivery system configured to deliver feed received from outside the container to each tray repeatedly over a period of time. The rearing module may include a heating, ventilation, and air conditioning system for controlling the temperature of the interior of the container.

A stack may comprise a set of interlockable trays. A stack may comprise a tray carrier, such as a rack (for example in the form a tray trolley), and one or more (preferably a plurality of) trays disposed (e.g. inserted or placed) in the tray carrier.

The tray handling system may be arranged to move the trays or the stack of trays around a closed path, which may be rectangular. The stack may include wheels or casters on the bottom of the trays, bottom-most tray of a stack of interlocked trays or racks. The tray handling system may include ball transfer units and/or rollers. The tray handling system may include guide rails.

The rearing module may be arranged such that the trays or the stacks of trays are insertable into and removable from the tray handling system using a forklift truck, on rollers or casters or other form of transporting system.

The rearing module may comprise one or more arms for delivering feed, wherein each arm is arranged such that a corresponding tray passes under the arm.

The container may take the form of a shipping container, such as a nominal 20-foot (6.1 m) or 40-foot (12.2 m) shipping container.

According to a fourth aspect of the present invention there is provided a method of installing a system for rearing insect larvae. The method may comprise providing a waste management module configured to receive organic waste and to convert the organic waste into a feed for insect larvae, providing at least one rearing module configured to handle a plurality of trays of larvae and to provide the feed to the trays and arranging for feed to be supplied from the waste management module to each of the at least one rearing modules. Arranging for the feed to be supplied from the waste management module to each of the at least one rearing modules may comprise installing a tube or respective tubes for delivering feed running from the waste management module to each of the at least one rearing modules.

Providing the waste management module may include delivering, for example using a lorry or truck, the waste management module substantially prefabricated to a site.

Providing the at least one rearing module may include delivering, for example using a lorry or truck, each rearing module substantially prefabricated to a site.

According to a fifth aspect of the present invention there is provided a method of operating a system for rearing insect larvae. The method comprises a waste management module receiving organic waste and converting the organic waste into a feed for insect larvae and delivering the feed to the insect larvae to at least one rearing module via a tube or respective tube and each rearing module moving trays or stacks of trays and repeatedly delivering feed to the trays or the stacks of trays.

According to a sixth aspect of the present invention there is provided a monitoring system for an insect larvae rearing system.

The system may include, in a rearing module, a set of one or more sensors and/or cameras configured to capture data relating to the status of the rearing module and/or of equipment within the rearing module and/or of larvae in the rearing module, and a control system configured to receive and process the data. The control system may be configured to transmit the data to a remote location. The control system may be configured in dependence upon a detection of data matching a predetermined criterion to signal the criterion or other data to a local or remote location or be configured to automatically correlate received data to a set of one or more predetermined criteria and transmit the criteria or other data to a remote or local location. The system may include actuators and/or switches and/or control units in the rearing system configured to receive control signals from the control system. The system may include interface(s) to wired and/or wireless (e.g. cellular or wireless LAN) network for transmitting signals to and/or receiving signals from a remote location.

The system may include, in a waste management module, a set of one or more sensors and/or cameras configured to capture data relating to status of the waste management module and/or of equipment within the waste management module and/or of organic waste in the waste management module and/or feed generated from the organic waste, and a control system configured to receive and process the data. The control system may be configured to transmit the data to a remote location. The control system may be configured in dependence upon a detection of data matching a predetermined criterion to signal the criterion or other data to a local or remote location or be configured to automatically correlate received data to a set of predetermined criteria and transmit the criteria or other data to a remote or local location. The system may include actuators and/or switches and/or control units in the waste management system configured to receive control signals from the control system. The system may include interface(s) to wired and/or wireless (e.g. cellular or wireless LAN) network for transmitting signals to and/or receiving signals from a remote location.

The sensors may include one or more temperature sensors, one or more humidity sensors, one ore more gas sensors, one or more motion sensors, one or more acceleration sensors, one or more gyroscopic sensors, one or more weight sensors and/or one or more visual recognition sensors, such as cameras or video recording equipment cameras.

According to a seventh aspect of the present invention there is provided an insect larvae rearing and consumption system comprising a system for rearing insect larvae of the first aspect and an insect larvae consumer installation.

The insect larvae rearing system may be located at the same site as or near to (<5 km) the insect larvae consumer installation. The insect larvae rearing system may be located at a different site from or far from (>5 km) the insect larvae consumer installation. The insect larvae rearing system may serve more than one insect larvae consumer installations, for example, more than one farm. A plurality of farms may be clustered (for example, within a radius of 5 km). The insect larvae rearing system may be located at one of the plurality of farms.

BRIEF DESCRIPTION OF THE DRAWINGS

Certain embodiments of the present invention will now be described, by way of example, with reference to the accompanying drawings, in which.

DETAILED DESCRIPTION OF CERTAIN EMBODIMENTS

Insect Larva Rearing System Overview

Figure 1:
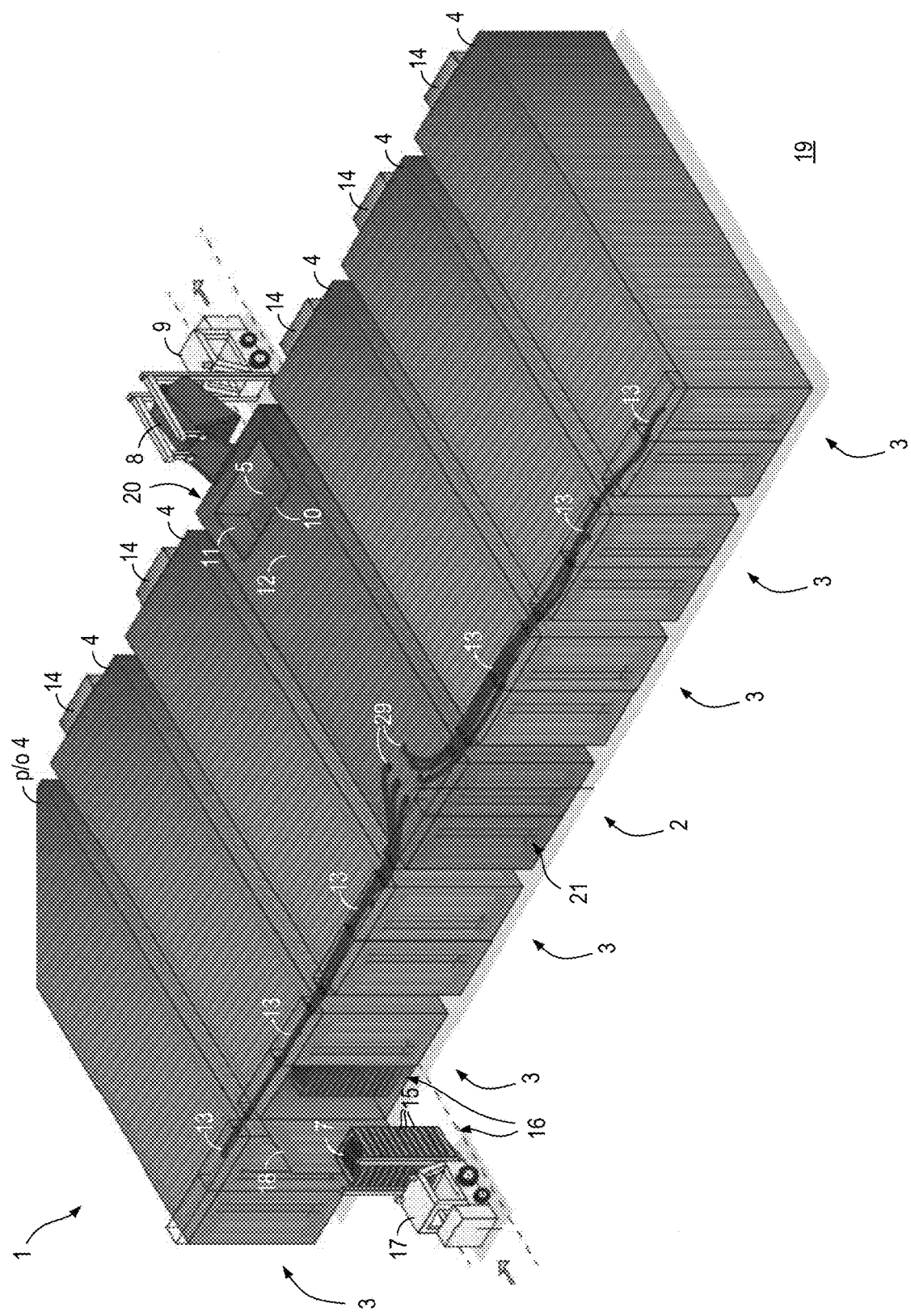
FIG. 1 is a schematic perspective view of a larvae rearing farm or factory.

Referring to FIG. 1, an insect larvae rearing system 1 (herein simply referred to as a "rearing system", "farm" or "factory") is shown. The rearing system 1 comprises a set of modules 2, 3, each module 2, 3 housed in a respective housing 4. Each housing 4 preferably takes the form of a transportable container, in particular a standard-sized, general-purpose shipping container, such as a nominal 10-foot (3.0 m), 20-foot (6.1 m) or 40-foot (12.2 m) shipping container (also referred to as a "freight container" or "intermodal container"). Actual length of a shipping container may vary from its nominal length by up to 10%.

The modules 2, 3 include a module 2 of a first type for processing organic waste (which may or may not be regarded as waste as such), for example food waste, pre-consumer food waste or by-products, such as potatoes, onions and other agricultural waste residues or parts thereof, other forms organic biomass which can be used as feed, such as brewers grains or low-value feed-stock, and/or optionally other forms of suitable waste, such as manure, to prepare a feed 6 (or "larval food") for insect larvae 7, and at least one module 3 of a second type in which larvae 7 are kept, fed and harvested, in environmentally-controlled conditions, to produce grown larvae 7 which can be used as animal feed. The larvae 7 preferably take the form of black soldier fly larvae, although other types of insect larvae can be used, such as larvae of mealworms, crickets, waxworms or housefly. The first and second types of modules 2, 3 are herein referred to as "waste management modules" and "rearing modules" respectively.

Organic waste 5 can be delivered to a waste management module 2, for example, in bins or other suitable containers 8 delivered by a suitable vehicle 9, such as a forklift truck or tipper, and into a hopper 10 which lies under or behind a hole 11 cut in a wall or roof 12 of the waste management module 2 or disposed on top of the waste management module 2. The feed 6 is pumped from the waste management module 2 to rearing modules 3 through one or more tubes 13 for example which may include hoses and/or pipes. Each rearing module 3 is provided with a heating, ventilation, and air conditioning (HVAC) unit 14. As will be explained in more detail later, larvae 7 are housed in trays 15 arranged in stacks 16, and larvae 7 can be delivered and removed, stack-wise, for example using a forklift truck or other a suitable vehicle 17, via doors 18. The trays 15 may be configured so as to form a self-supporting stack 18. For example, the trays may be interlockable. Trays 15 may be stacked in a rack, for example in the form of a tray trolley (not shown).

A third type of module 81 (FIG. 12) may be included for post-processing, for example, drying harvested larvae using a belt dryer, although this type of module may be integrated into the second type of module, or omitted. The third module 81 (FIG. 12) may also include a sieve or some other mechanism for separating the larvae from the residual organic material in the tray comprising undigested food waste and insect 'manure' (collectively referred to as "frass").

The factory or farm 1 is modular, whereby a waste management module 2 and at least one rearing module 3 are installed at a given site 19. Multiple factories or farms 1 can be installed at the same site, i.e. there may be at least two waste management modules 2. Thus, the number of each type of module 2, 3 can be scaled according to need and can be increased or decreased over a period of time. For example, modules can be added according to seasonal needs, e.g. farms which grow grain, fruit or vegetables, which may take the form of root, a beet, a bulb (such as onion), a tuber (such a potato). One waste management module 2 can be provided for one or more rearing modules 3, preferably two or more rearing modules 3 and more preferably for between four and ten rearing modules 3. Furthermore, the factory or farm 1 can form part of a distributed (or "decentralized") network of farms or factories across a geographical area, such as a country or group of countries or a region (of a country or of a group of countries, such as the European Union), especially if transportable containers 4 are used. This can help to reduce the distance over which organic waste 5, such as food waste, is transported to the farms or factories 1, thereby helping to decrease the amount of energy and CO2 emissions used to transport the waste and other transport costs (compared to a centralized farm or factory serving the same area).

In some embodiments, the waste management module 2 may be omitted and, instead, feed 6 is provided in intermediate bulk container, for example, having capacity of 1,000 litres and which is pumped into rearing modules 3 by a pump (not shown) or, the container can be elevated, fed by gravity.

Interfaces

Referring still to FIG. 1, after the farm or factory 1 has been installed and set up by an installer (not shown), organic waste 5 can be loaded by an operator (not shown) into the top of one end 20 of the waste management module 2, which in this example, is in the middle of a row of modules 2, 3. Once the organic waste 5 has been processed in the waste management module 2, it is pumped into each rearing module 3. When a rearing module 3 is ready for harvesting, one or more stacks 16 of trays 15 containing mature larvae ("mature trays") can be exchanged for a corresponding number of stacks(s) 16 of young larvae 7 or fly eggs ("fresh trays"). The process and equipment may be monitored remotely from a central facility (not shown) serving the factory or farm 1 or a network of factories or farms 1. A separate facility (not shown), such as the central facility (not shown), can cultivate insect eggs and/or young larvae 7 for supply to the farm or factory 1. Insect eggs and/or young larvae 7 can, however, be cultivated locally, i.e. at the site 19 of the farm or factory 1. An additional module (not shown) may be provided for breeding the larvae into its final mature insect (in this case, 'adult fly') phase.

Installation and Setup

Modules 2, 3 for a farm or factory 1 can be delivered and setup onsite with a truck having integrated loader crane (not shown). The modules 2, 3 are preferably arranged in a row or line adjacently to each to other. The modules 2, 3 may be stacked. This can help reduce the footprint of the farm or factory 1. Each container 4 is leveled with jack stands or similar leveling equipment, or placed onto a leveled concrete slab (not shown). The modules 2, 3 are connected to a three-phase power supply (not shown) and a water exhaust hose (not shown) is connected between the waste management module 2 and an onsite foul water drain (not shown).

Feed Transfer to Rearing Module

Once organic waste 5 has been processed, transferred and stored at the opposite end 21 of the waste management module 2, it is pumped to the rearing modules 3.

Figure 2:
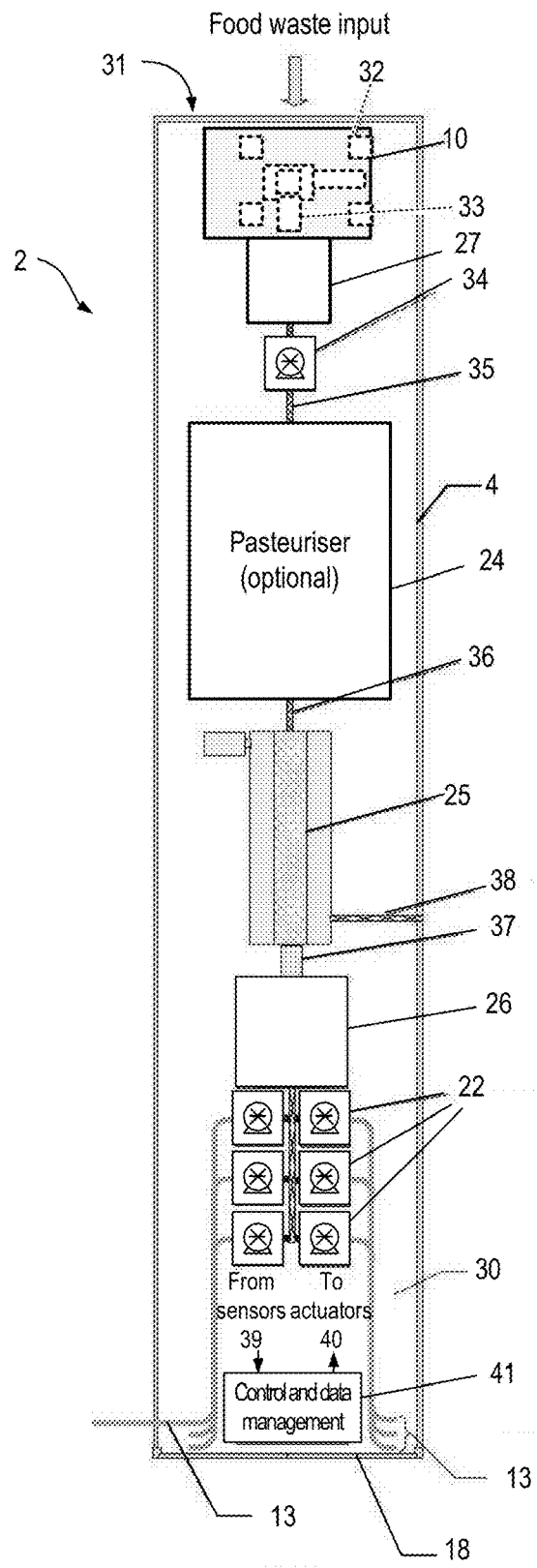
FIG. 2 is schematic block diagram of a waste management module.

Referring also to FIG. 2, each rearing module 3 is served by its own pump 22, housed within the waste management module 2. Alternately, fewer pumps or even one pump may be provided and the tubes may include valves. However, using individual pumps can help to provide better control. An individual feed pump 22 can be initiated automatically by a control signal (not shown) sent from the rearing module 3 to the waste management module 2. The feed 6 in the form of slurry is transported from the pump 22 to the rearing container 3 via a (e.g. 5-cm) tube 13 running between the tops of the modules 2, 3.

Larvae Exchange

Figure 3:
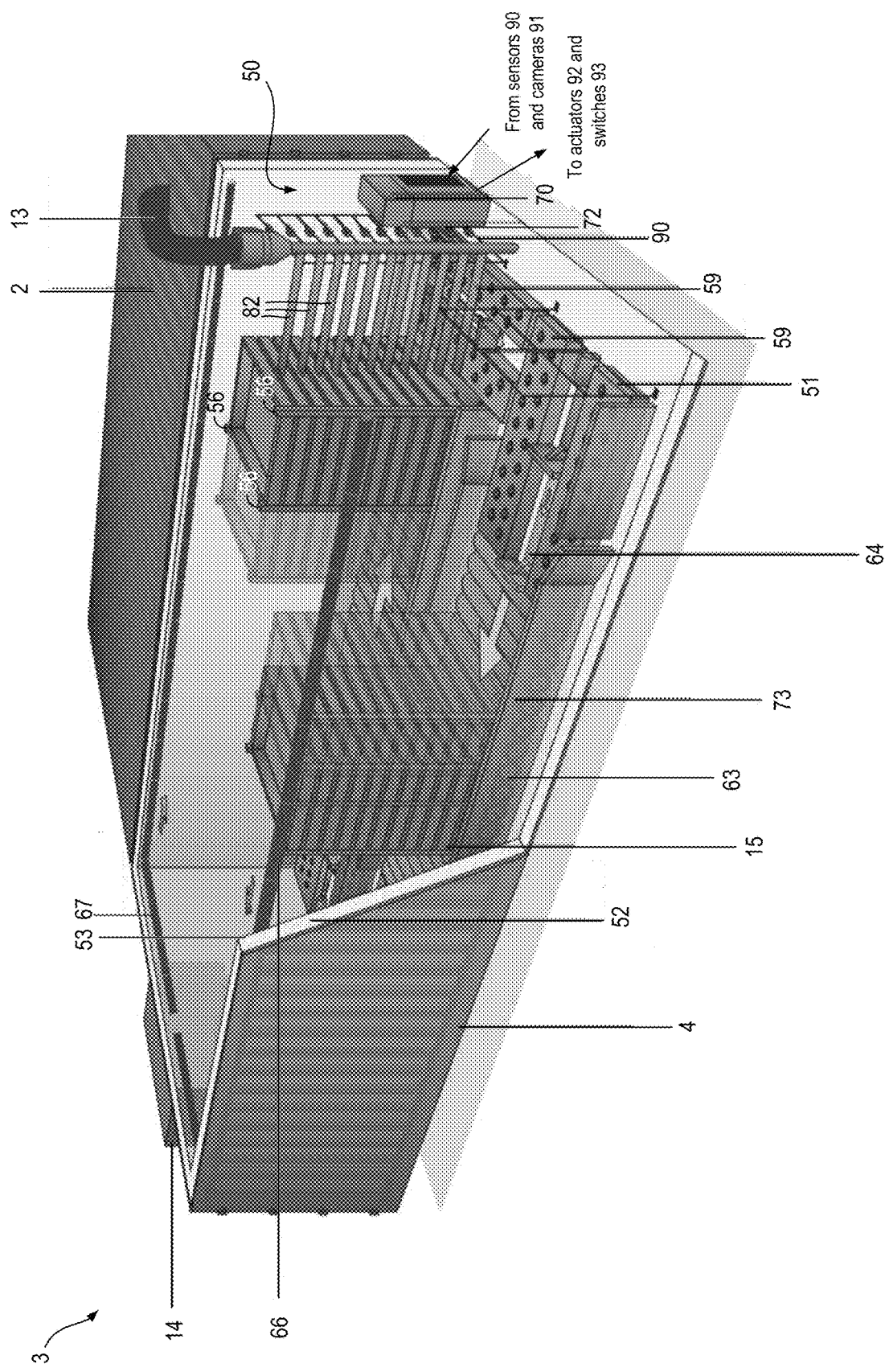
FIG. 3 is a perspective, partial cut-way view of a rearing module.

When the larvae 7 in a rearing module 3 reach a minimum maturity for harvest, the module 3 may automatically signal this finding to the central (not shown) and an operator (not shown) with a lorry (not shown) of replacement trays 15 may be dispatched to factory or farm 1. On arrival, the operator opens the container doors 18 and internal rack gates 51 (FIG. 3). One or more mature stacks 16 can then be exchanged for fresh stack(s) 16 on a "one-out-one-in" basis by forklift 17 and the module's control system.

Monitoring

The status of every module 3 in service can be monitored, for example, remotely from the central facility (not shown) or locally (i.e. at the site 19). By using data collected from a set of sensors and/or cameras (not shown), an operator and/or a licensor can determine if the equipment in the modules 2, 3 and the larvae contained in modules 3 are behaving as expected. For instance, there might be a change in flowrate resulting in a bottleneck if, for example, the larvae 7 are hungry, diseased or reach maturity, i.e. the larvae 7 become ready to harvest.

If a module 2, 3 is flagged as having a potential problem, an operator can carry out an inspection. This can provide predictive maintenance and/or improved disease control within modules 2, 3.

Waste Management Module 2

Referring still to FIGS. 1 and 2, the waste management module 2 can be housed in a suitably-modified shipping container 4. Organic waste 5 is supplied from bins 8 using a bin-tipping loading mechanism (not shown) or forklift 9. The organic waste 5 shredded, pumped through an optional pasteurizer 24 and de-waterer 25, and then stored in a hopper 26 ready for pumping to the rearing module 3. Hoppers (not shown) can be provided upstream and downstream of the loading mechanism 23 to buffer the difference in flowrates between the equipment.

Shipping Container

As explained earlier, a standard-sized shipping container 4, for example a 40-foot (12.2 m) shipping container 4, can be modified for use as a waste management module 2.

An opening 11 is cut into the top 12 of the shipping container 4 for the input hopper 10. Several other, smaller openings 29 are cut into the top 12 for the feeding hoses 13. The container 4 is internally lined with stainless-steel sheets 30 for ease of cleaning. An opening (not shown) is cut in the rear wall 31 for a three-phase power socket (not shown). Another opening (not shown) is cut into the rear wall 31 for the exhaust water.

Loading Mechanism

If no forklift attachment is available onsite, an externally-mounted loading mechanism (not shown) in the form of a bin tipper can be provided for each waste management module 2. The loading mechanism (not shown) is arranged to tip a bin 8 or other form of waste container of input organic waste 5 into the first hopper 10, located in the roof of the waste management module 2.

Shredder

The organic waste 5 from the first hopper 10 falls under gravity into a shredder 32. The shredder 32 shreds the organic waste 5 into the smaller particle sizes for pumping, de-watering and feeding. A suitable shredder 32 can take the form of a model TM8500 available from Franklin Miller®

(Livingston, New Jersey, USA). Once shredded, the organic waste 5 falls under gravity via chute 33 into a second hopper 27.

Wet Pump

The shredded organic waste 5 is pumped from the second hopper 27 through the pasteurizer 24 (if used) and into the de-waterer 25 using a positive displacement pump 34. The positive displacement pump 34 can take the form of a peristaltic pump, a rotary lobe pump, or sine pump or screw pump. A sine pump is preferred since it may be more reliable if stones are inadvertently introduced into the system. An example of a suitable sine pump is a Certa 250 pump available from Watson-Marlow (Falmouth, Cornwall, UK). The organic waste 5 is transported through 2-inch (5-cm) 16-bar (1,600 kPa) hose(s) 35, 36.

Pasteurizer

The shredded organic waste 5 may be pumped through a pasteurizer 24 to remove certain bacteria that are harmful to larvae. The pasteurizer 24 may take the form of a scraped surface heat exchanger, a microwave or a steam screw. An example of a suitable pasteurizer is a continuous microwave pasteurizer available from Advanced Microwave Technologies (Roslin, Edinburgh, UK). As explainer earlier, however, a pasteurizer 24 need not be used.

De-Waterer

To reduce the water content of the feed 6 so that it lies within a range acceptable for larvae consumption, the shredded organic waste 5 is dewatered using a de-waterer 25. An example of a suitable de-waterer is Voran EBP650 Belt Press available from Voran Maschinen GmbH (Pichl bei Wels, Austria).

Once the organic waste 5 is dewatered, it is dropped, via a chute 37, into the third hopper 26, ready to be used as feed 6. Excess water is exhausted out of the container 4 via exhaust hose 38 into a drain suitable for foul water (not shown).

Hoppers

The minimum size of the hoppers need to avoid a system bottle neck can be estimated by modeling. In this example, the first hopper 10 (i.e. the hopper which receives organic waste from a bin 8) has a 12,000-litre capacity, the second hopper 26 (i.e. the hopper which holds feed 6 ready to be pumped to the rearing modules 3) has a 1,000-litre capacity and the third hopper 27 has a 50-litre capacity.

Additional hoppers or containers may be included for storing feed before it is delivered for a period of time, for example, for a day or longer.

The feed 7 may take the form of a slurry or wet solid.

Feeding Pumps

Each rearing module 2 is delivered feed 6 by an individual pump 22 and a hose 13. The pumps 22 are housed in the waste management module 2 and are gravity fed by the third hopper 26. After de-watering, the feed 6 can be viscous and therefore difficult to pump. Therefore, pumps, for example in the form of sine pumps, are used which can handle viscosity of 104 mPa·s (which is similar to mash potato). A suitable type of pump is a Certa 100 pump available from Watson-Marlow (Falmouth Cornwall, UK). This type of pump operates best when powered by a three-phase supply. The organic waste 6 is carried between the third hopper 26, pump and rearing module by 2-inch (5-cm) 16 bar (1,600 kPa) hoses 13.

Sensors and Control

Actuators and switches 39 and sensors 40 can be used to enable process automation and remote monitoring. A list of sensors 40 is set out in Table 1 below. The sensors 40 are read by a control and data management module 41 which can connect to a backend server (not shown) at the central facility (not shown) via IP over a mobile cellular network (not shown).

The control and data management module 41 in the waste management module 2 can take the form of a PLC system or can run on an embedded platform.

Maintenance

All equipment may be IP66 rated and the container wall lined with stainless steel sheets 30 to enable cleaning with a pressure washer. The internals of the process equipment can be periodically cleaned with water and a cleaning agent to remove build-up of organic waste with frequency to be determined by testing (e.g. quarterly).

TABLE 1

| Sensor | Location | Purpose |
| --- | --- | --- |
| Loading mechanism switch | Loading mechanism | Starts loading mechanism |
| Load cell | First hopper 10 | Evaluate hopper level Deactivates shredder 32 if empty Deactivates loading mechanism if full |
| Current meter | Shredder power supply Wet pump power supply Pasteuriser power supply De-waterer power supply Feed pumps power supply | Evaluates equipment duty |
| Resistive level meter | Third hopper 27 | Evaluate hopper level De-activates feed pump if empty De-activates wet pump, pasteuriser and de-waterer |
| Resistive level meter | Second hopper 26 | Evaluate hopper level De-activates wet pump if empty De-activates shredder if full |
| Thermocouple | Inside container | Evaluates internal temperature Activates space heater if sub zero |

Rearing Module

Figure 4:
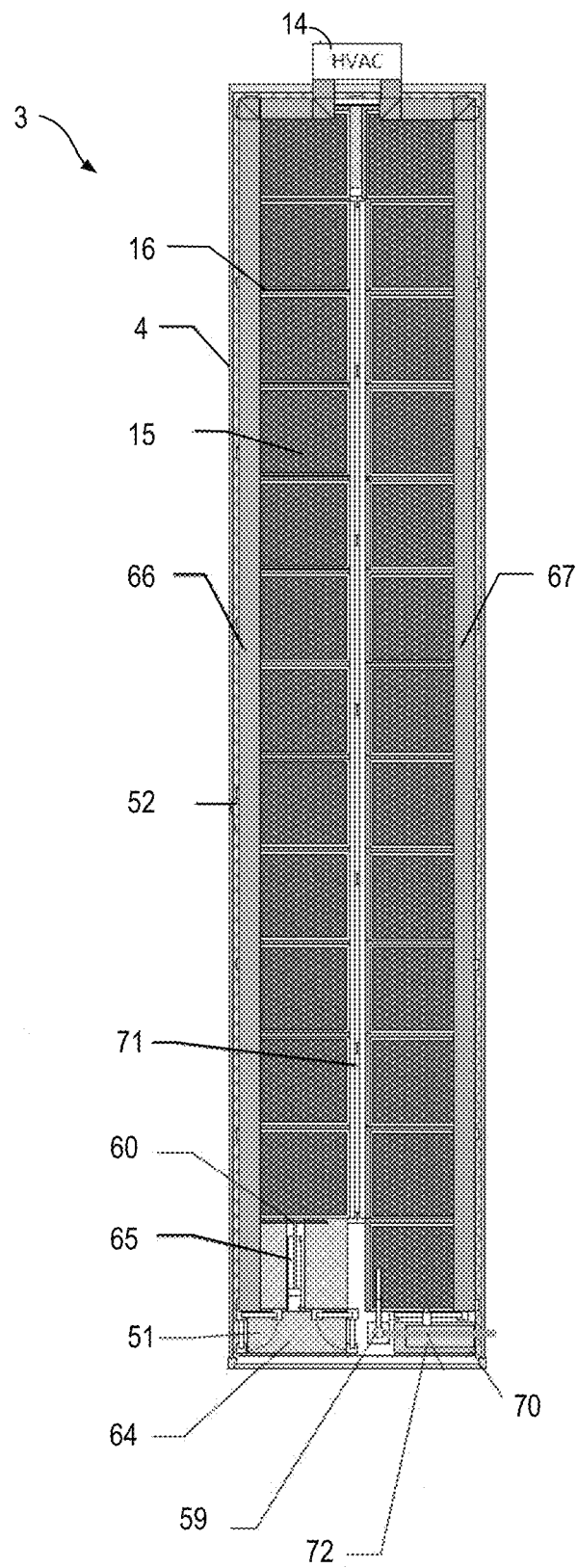
FIG. 4 is a plan view of a rearing module.

Referring to FIGS. 3 and 4, the rearing module 3 can be housed in a standard-sized shipping container 4, for example a 40-foot (12.2 m) shipping container 4. The shipping container 4 is climate controlled using an HVAC unit 14.

In each rearing module 3, the larvae are housed in twenty-five stacks 16, each stack 16 holding or consisting of ten vertically-stacked trays 15. Fewer or more stacks 16 can be used and/or fewer or more trays 15 can be used in each stack 16. The stacks 16 are continuously or periodically moved around an internal perimeter of the container 4.

Feeding and visual inspection occurs in one corner 50 of the container 4. Inspection may occur in a different location (for example, a different corner) to feeding. Loading and unloading occurs by opening gates 51 at the front 21 of the container 4.

Shipping Container

As explained earlier, a standard-sized shipping container 4, for example a 40-foot (12.2 m) shipping container 4, can be modified for use as a rearing module 3. Internal walls, ceiling and floor may be clad with insulation 52 and stainless-steel sheets 53. An HVAC unit 14 is mounted to the rear wall of the container 4. An opening (not shown) is cut in the rear wall for a three-phase power socket (not shown). Another opening (not shown) is cut the roof for the feed hose 13.

Trays

The larvae are segregated into trays 15 to control disease and improve feeding efficiency. Each tray 15 has dimensions of 0.7 m×1.0 m×0.1 m. The trays 15 may be formed from a suitable plastics material formed, for example, by vacuum casting. The trays 15 may take the form of Dolav® Box Pallet Type 800 Solid.

Stacks

Figure 5:
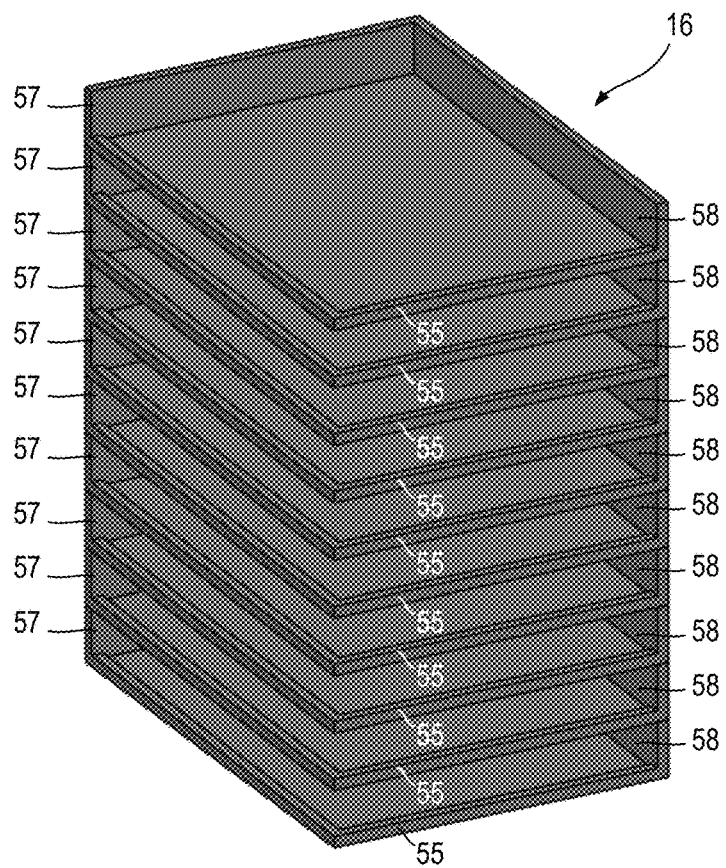
FIG. 5 is a schematic perspective view from above of a stack of interlocking trays.

Referring also to FIG. 5, each stack 16 may be formed by trays 15 forming shelves 55 and defining three vertical struts or pillars 56 (best shown in FIG. 3) and two side walls 57, 58 which form an 'L'-shape (in plan view). The side walls 57, 58 may be perforated to aid circulation of air. Alternatively, a stack 16 may be formed using a tray carrier such as a rack (not shown), for example in the form of a tray trolley comprising shelves joined by three vertical structs or pillars). The rack may be formed from aluminium, stainless steel, or other suitable durable material.

Figure 6:
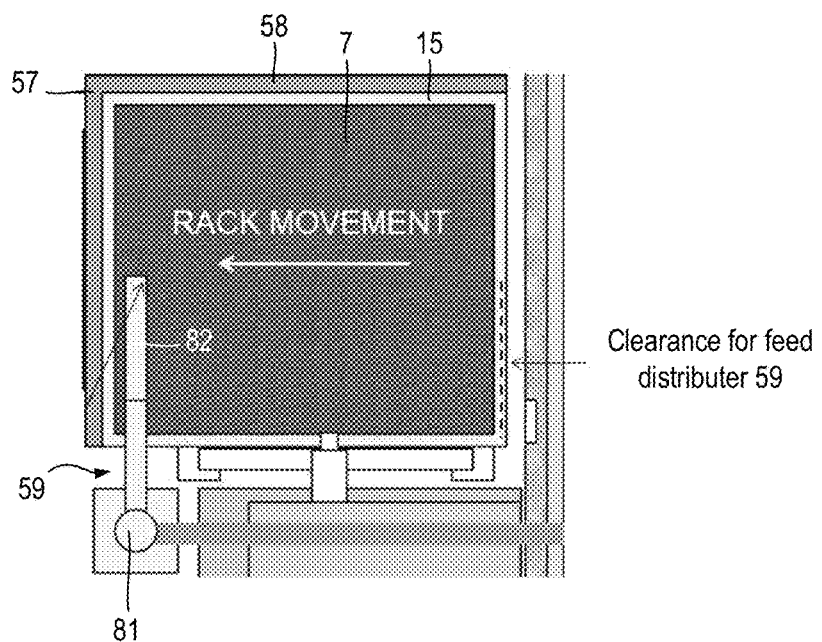
FIG. 6 is schematic plan view of a feed distributer and a stack of interlocking trays.

Referring also to FIG. 6, the stack 16 has only three vertical struts (i.e., one corner does not have a strut to allow a feed distributer 59 to access as the stack 16 moves around the container.

Figure 7:
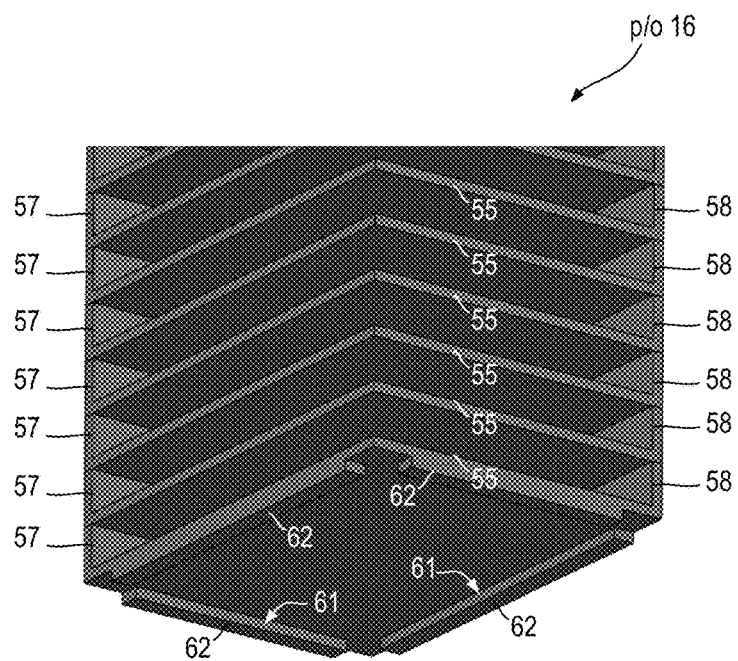
FIG. 7 is a schematic perspective view from below of a stack of interlocking trays.

Referring also to FIG. 7, to move the stack 16, hydraulic actuators 60 (or "plate") push on an inside surface 61 of a depending boss or ridge 62 running along each of the sides of the bottom of the stack 16. Other forms of conveyance systems may be used, such as conveyers, telescopic pistons and the like.

Stack Carrier Movement

Figure 8:
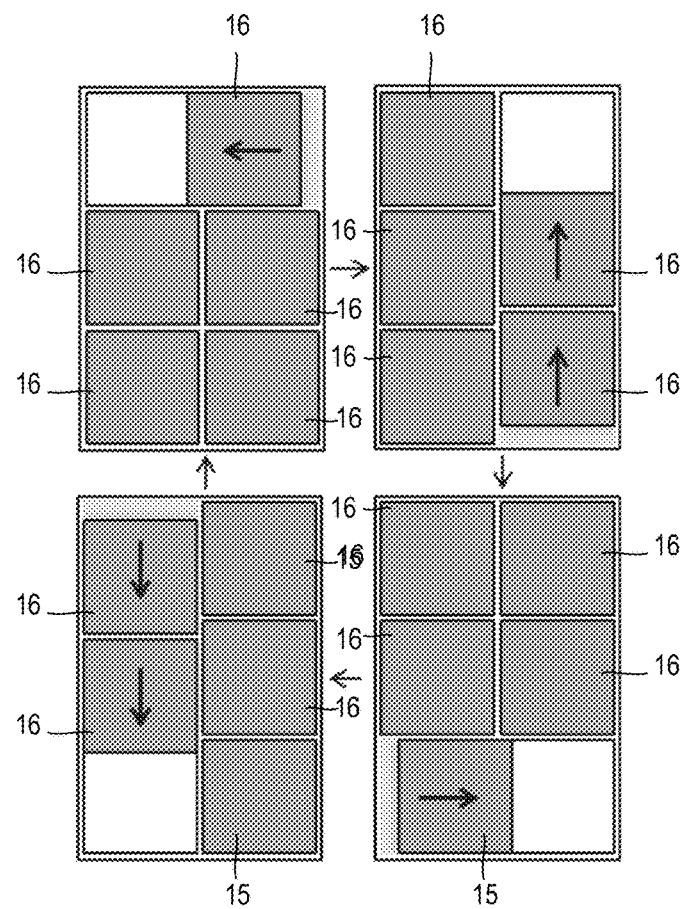
FIG. 8 schematically illustrates stack movement.
Figure 9:
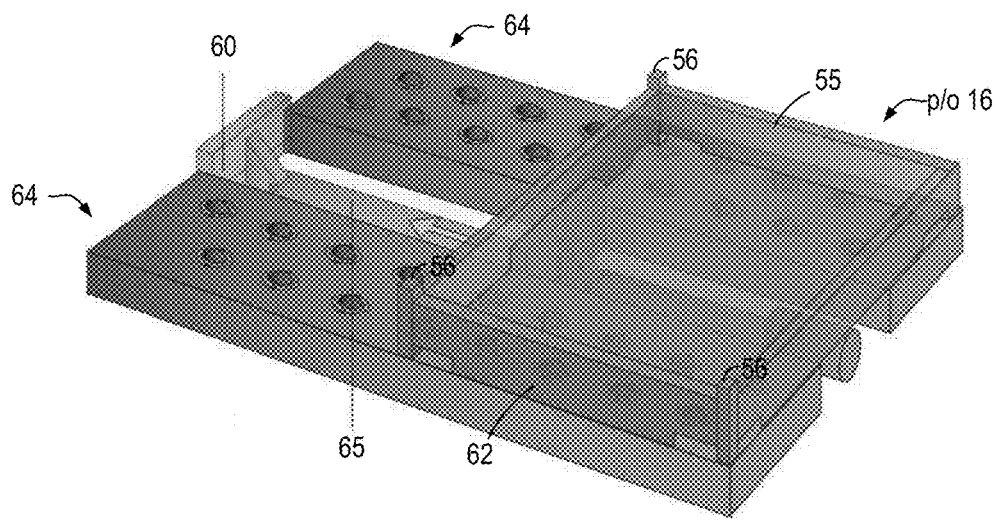
FIG. 9 is a perspective view of a ball transfer unit, which includes a ram and a hinged actuator plate.

Movement of stacks 16 within the module 3 will be described with reference to FIG. 8.

Referring to FIGS. 3, 4, 8 and 9, the stacks 16 move around the internal perimeter of the container 4 on roller floor 63 along the sides of the container 4 and four ball transfer units 64 in each corner of the container 4, each unit provided with a hydraulic ram 65 having a hydraulic plate 60 in each corner. Other forms of support and drive systems may be used such as rollers and pneumatic arms or driven rollers. Alternatively, the bottom of the stacks 16 (i.e. the bottom of the bottom-most tray or the bottom of a tray carrier) may have wheels or casters.

The container 4 is packed with stacks 16 of trays 15, except for one empty space. The hydraulic rams 65 in each corner take turns to shunt the stacks 16 into the empty space and thus continually moving the stacks 16 around the container 4.

Figure 10A:
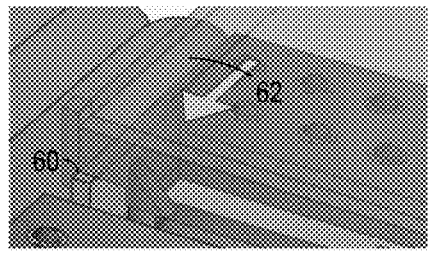
FIGS. 10A and 10B a perspective views showing action and retraction of the hinged actuator plate.

Referring also to FIG. 10A, the interface between each hydraulic cylinder and the stacks it is pushing is a sprung plate 60 (or "flap") which is hinged along its lower edge. When pushing a stacks 16, the plate 60 is rigid and applies the required force on the inside edge of the boss 62 on the bottom side of the stacks.

Figure 10B:
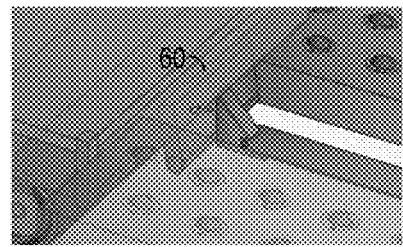

Referring also to FIG. 10B, when the ram 65 is retracting to engage with the next stacks it is able to deflect (i.e. fold) under the boss 62 of one stack 16 to re-engage with the inside face of the next stacks.

The hydraulic rams 65 are driven by a combined pump and control unit 70. The unit 70 actuates solenoid valves (not shown) to extend and retract each ram 65 in turn. The force, pressure, flowrate and energy requirements of the hydraulic system are set according to throughput.

To guide the stacks 16 and prevent them crashing into each other, a guide rail 71 is mounted to the perimeter and down the centre of the container 4.

Feeding

When feed is required, the rearing module's control module 72 sends a request to the waste management's control module 41 (FIG. 2) to activate the pump 22 (FIG. 2). The pump 22 (FIG. 2) transfers the feed 6 from the second hopper 26 (FIG. 2) to a feed distributer 59 via hose 13.

Figure 11:
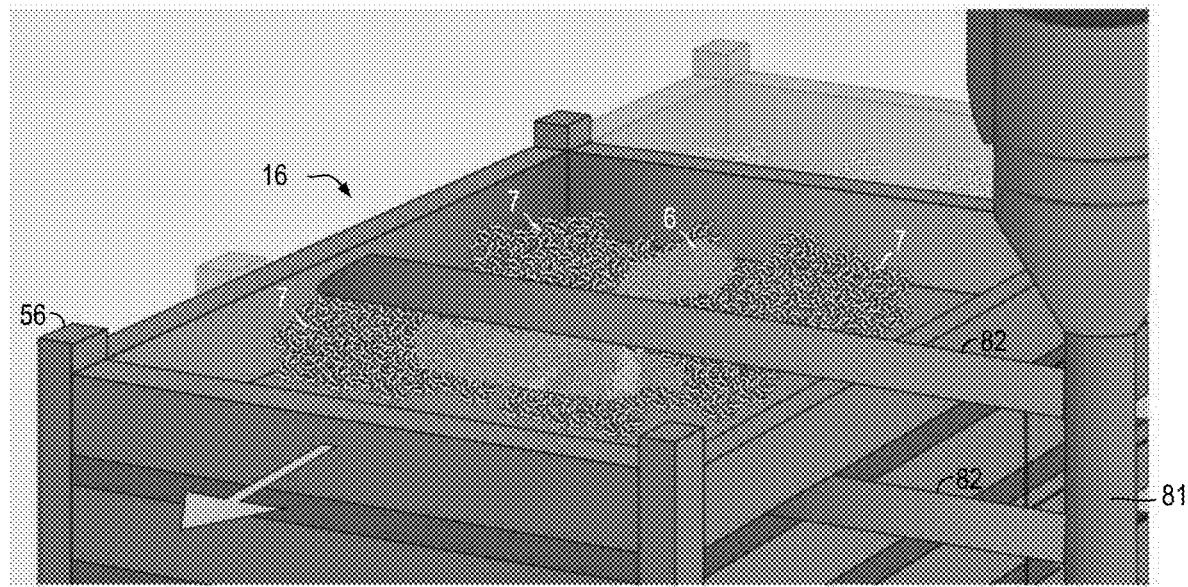
FIG. 11 is a perspective view of a tray and a feed distributer.

Referring in particular to FIGS. 3 and 11, the feed distributer 59 comprises a vertical pipe 81 and vertically-spaced, horizontally-extending pipes 82 (or "arms") extending from the vertical pipe over each tray 15 in a stack 16. Each horizontal pipe has a longitudinal, slot-like opening, or series of nozzles or sprayers so that feed 6 is distributed evenly over the tray 15 as the stack 16 is moving.

As the stack 16 only has three uprights 56, the arms 82 of the feeding distributer 59 can pass through the stack 16 at the end of a feed.

Climate Control

The HVAC unit 14 mounted to the end of each rearing module 3 pumps fresh air down ducting 66 which vents into the interior of the container 4, keeping the larvae at approximately 27° C. The unit 14 removes excess carbon dioxide and ammonia. As racks 15 are moved around the container 4 they are exposed to fresh air. Hot, moist air is vented out of the container 4 through a return duct 67 on the opposite edge of the container 4. The container is insulated with an internal PIR (polyisocyanurate) cladding 52 and sprayed foam underneath.

Loading and Unloading

Trays 15 or stacks 16 (which may include a rack or other form of tray carrier) are exchanged at the front door 18 of the rearing module container 4. Inside the module 3, the guide rail can be opened up to access the racks. A process of loading and unloading will now be described:

An operator (not shown) opens the guide rail gate (step S1). When the gate 51 is opened, the system goes into "loading/unloading mode". A stack 16 of mature trays 15 is removed by forklift 17 (FIG. 1) (step S2). A stack of fresh trays 15 is loaded into the module by forklift 17 (FIG. 1) (step S3). The operator interacts with the control and data module 72 to expose the next mature rack (step S4). This process (i.e. steps S2 to S4) is repeated for example, in this case, 24 times. The loading and unloading process may take one to two hours.

Sensors and Control

The rearing module 1 includes sensors 90 and cameras 91, and sensors 92 and switches 93 to enable process automation and remote monitoring of the larvae 7. The sensors 90 are read by a control and data management module 72 which connects to the backend server (not shown) via IP over the mobile cellular network (not shown).

The backend server (not shown) can then provide a web interface (not shown) to an operator (not shown) on site using a tablet or smart phone (not shown) for control of the loading and unloading process and for other maintenance purposes.

Table 2 below lists sensors and cameras 91 deployed in the rearing unit 3.

TABLE 2

| Sensor | Location | Purpose |
| --- | --- | --- |
| Camera | One camera for each tray Next to feeding station | Visual evaluation of larvae condition e.g. healthy, diseased, mature, hungry |
| Bluetooth enabled thermocouple | One in each tray | Measures temperature of larvae |
| Thermocouple | Container roof space & container floor space | Measure container temperature |

TABLE 2-continued

| Sensor | Location | Purpose |
|---|---|---|
| Hygrometer | Container roof space & container floor space | Measure container humidity |
| $CO_2$ sensor | Container roof space & container floor space | Measure $CO_2$ levels |
| Current meter | Hydraulic pump power supply HVAC power supply | Evaluates pump duty Evaluates HVAC duty |

The use of a temperature sensor in each tray can be used to collect increased amounts of data about the larvae conditions. Fewer temperature sensors may be used.

Maintenance

The equipment may be IP66 rated and the container walls lined with stainless steel sheet (not shown) to enable cleaning with a pressure washer. The internals of the feeding equipment can be periodically cleaned with water and a cleaning agent to remove build-up of organic waste with frequency to be determined by testing (e.g. quarterly).

Location

Figure 12:
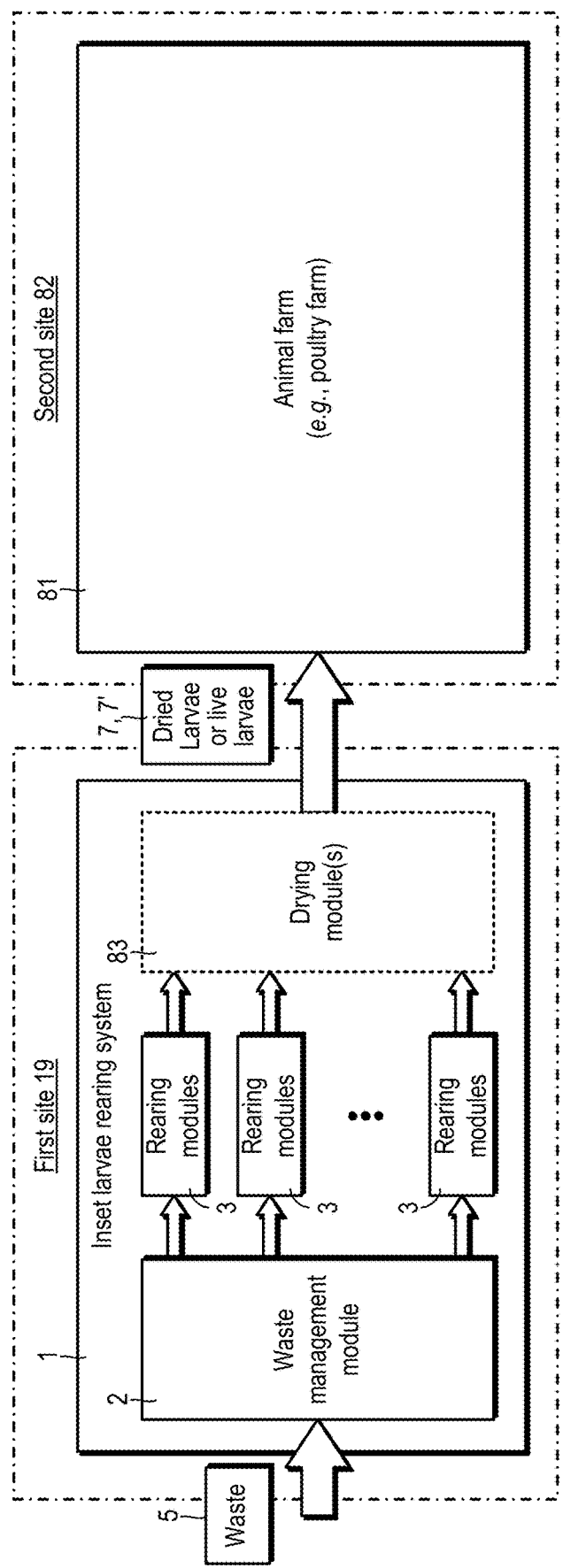
FIG. 12 illustrates a first arrangement whereby a larvae rearing farm and an animal farm are located at geographically spaced sites.

Referring to FIG. 12, a first arrangement of insect larvae rearing farm 1 and an animal farm 81 is shown. The animal farm 81 can take the form of a poultry farm. The insect larvae farm 1 and animal farm 81 are located at respective geographically spaced apart sites 18, 82. For example, the two sites 18, 82 may be separated by at least 5 km. There may be several animal farms 81 served by one insect larvae farm 1. This arrangement can be used to help minimize transportation of waste 5. Thus, the insect larvae rearing farm 1 may be located where waste 5 is generated, for example, at an arable farm. Such waste 5 can be referred to as "on-site generated waste" or simply "on-site waste". Alternatively, it may be delivered, for example, in trucks, from other locations. Such waste 5 can be referred to as "off-site generated waste" or simply "off-site waste. Live larvae 7 or dried larvae 7' can be transported between the insect larvae rearing farm 1 and the animal farm 81. As explained earlier, larvae 7 produced in the rearing modules 3 can be dried in the module 3 or be dried in a separate drying module 83.

Figure 13:
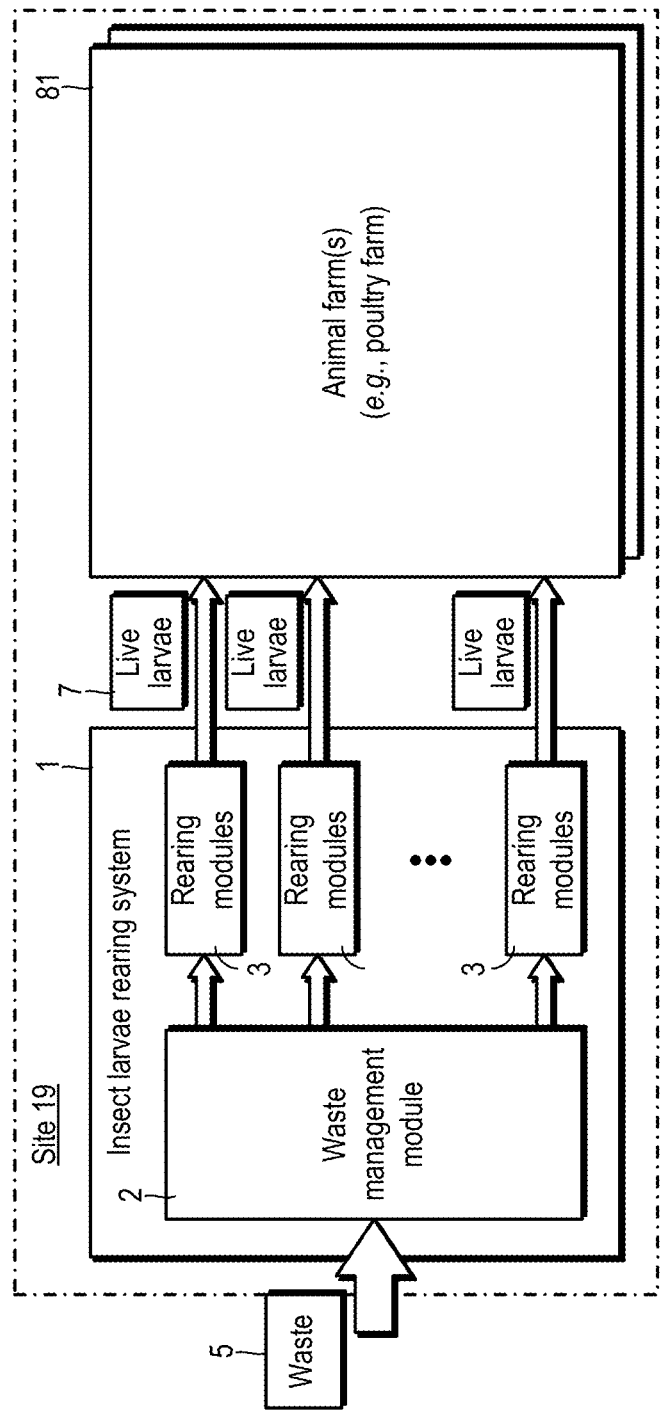
FIG. 13 illustrates a second arrangement whereby a larvae rearing farm and an animal farm are closely located or located one site.

Referring to FIG. 13, a second arrangement of insect larvae rearing farm 1 and an animal farm 81 is shown. In this case, the insect larvae farm 1 and animal farm 81 are located at the same site 18 or in close proximity (for example, less than 5 km). There may be one or more animal farms 81 served by one insect larvae farm 1. This arrangement can be used to help minimize transportation of larvae 7. Thus, the insect larvae rearing farm 1 may be located where larvae 7 are consumed. On-site or off-site waste may be used.

This can have the advantage that live insects are fed to chickens. Live insects are a superior feed for poultry as they are part of their natural diet: free range chickens eat live insects all the time. Moreover, certain compounds found in the casings of the larvae (which might ordinarily be lost if dried and processed) can have antimicrobial properties. Furthermore, live insects can enhance foraging behaviour and feeding on live insects is considered to contribute towards improved health and welfare of poultry.

Potential Advantages

The insect larvae rearing system 1 hereinbefore described can have one or more advantages. The system 1 can be picked up and dropped off easily, switching from one location to another when needed. The system is quick to install and commission. This can be useful for farming waste, the volume of which can vary seasonally. The system 1 can be tailored to customer needs. Handling 10,000 tonnes of waste per year or 100,000 tonnes of waste per year can be accommodated by using a different number of containers. The system 1 can be pre-fabricated in a factory and transported to point of use. This can reduce manufacturing costs. The system can be easy installed. The system can be exported to a developing country and/or remote locations. The system 1 can be automated or autonomous, for example, by including process control which employ machine learning to improve operation. This can be used to reduce the human input and so help to increase efficiency and lower operating expenses. The system 1 can reduce transportable volume of food waste (for example, by as much as 80%) by ameliorating a logistical bottleneck present in current setups in the waste industry. It can reduce greenhouse gas emissions resulting from less transportation. The system not only reduces barriers to entry in that it allows small-scale operators to run a small farm or factory, but also allows large-scale operators to run a large farm or factory. The system can be shipped to anywhere in the world.

Modifications

It will be appreciated that various modifications may be made to the embodiments hereinbefore described. Such modifications may involve equivalent and other features which are already known in the design, manufacture and use of industrial-scale food handling and processing equipment (such as hoppers, pumps, shredders, de-waterers, pasteurizers and the like), anaerobic digesters, insect rearing systems and component parts thereof and which may be used instead of or in addition to features already described herein. Features of one embodiment may be replaced or supplemented by features of another embodiment.

Other tray arrangements may be used.

In a "matrix" arrangement, trays may be stored statically in a matrix, each "slot" in the matrix has its own feeding tube and camera/sensors etc. The trays may be loaded and unloaded into the slots manually through side doors in the container.

In an "autostore" arrangement, a robot, traveling in the plane over the trays, can pick out trays as required (some columns are left empty to enable sorting) and takes them to a feeding/inspection station. Trays are loaded/unloaded at the loading/unloading station. In a "marble run" arrangement, trays can be stored on two sets of constantly moving (but slow) sets of rollers, some of which are driven. The rollers are arranged in a series of interconnected runs lying at two or more levels such that trays pass along one run, drop or pass down to a lower level and so on. The trays move around the container, periodically arriving at the feeding/inspection station. The trays are loaded/unloaded at the feeding station. In a "Paternosta" arrangement, the trays can be stored in several vertically-orientated carousels which keep the tray orientated horizontally throughout the rotation. A feeding pipe and inspection equipment is situated over each carousel; as the trays rotate they are individually inspected and fed. The trays are loaded and unloaded by opening both sides of the container and manually handling each tray off/on the carousels. In a "Jeeves" arrangement, trays are stored statically in two arrays. Between the arrays is a channel, down which a three-axis robot travels on a central rail. The robot collects individual trays and takes them to a feeding/inspection station at the front of the container. In a "butler" arrangement, trays are stored in stacks which are moved around the container by a robot, which can move underneath them. The stacks are taken to a multi-level feeding and inspection station in sequence. In an "inVia®" arrangement, an inVia® robot has a scissor lift which can be used to reach each tray on the stack. Using a suction cup, it pulls the tray onto itself and takes it to a feeding station.

Other forms of insect larvae can be used.

Intermediate bulk container (IBC) for example having a volume of 1 m³ may be connected to the rearing module to supply feed and/or larvae.

Although claims have been formulated in this application to particular combinations of features, it should be understood that the scope of the disclosure of the present invention also includes any novel features or any novel combination of features disclosed herein either explicitly or implicitly or any generalization thereof, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

The invention claimed is:

1. A system for rearing insect larvae, the system comprising:
    at least one feed container for a feed for insect larvae; and
    at least one transportable container comprising:
        a plurality of trays for larvae or a stack of trays for larvae,
        a feed distributer configured to deliver feed to one or more trays,
        an automated tray handling system configured to receive the plurality of trays for larvae or the stack of trays for larvae and configured to move the plurality of trays or the stack of trays periodically to or from the feed distributer, wherein the automated tray handling system comprises a control unit and further comprises a support and drive system and a conveyance system,
            wherein the support and drive system comprises a ball transfer unit, a driven roller, a pneumatic arm and roller, a tray having wheels or casters, or a tray carrier having wheels or casters, and
            wherein the conveyance system comprises a hydraulic ram, a hydraulic plate, a conveyor, a telescopic piston, a carousel, a suction cup, or a robot;
    a pump; and
    a tube running between the at least one feed container and the transportable container, wherein the pump and tube are configured to supply feed from the at least one feed container to the feed distributer of each of the at least one transportable container.

2. The system of claim 1, wherein each transportable container is a transportable container with a length of 10 feet, 20 feet, or 40 feet or a length shorter or longer than 10 feet, 20 feet, or 40 feet by up to 10%.

3. The system of claim 1, wherein each transportable container is a shipping container.

4. The system of claim 3, wherein the shipping container is an intermodal container or a freight container.

5. The system of claim 3, wherein the shipping container is a standard-sized 40-foot-long shipping container or a 20-foot-long shipping container.

6. The system of claim 1, wherein the system comprises at least two transportable containers, between 4 and 10 transportable containers, or between 10 and 20 transportable containers, wherein each transportable container comprises:
    a plurality of trays for larvae, or a stack of trays for larvae,
    a feed distributer configured to deliver feed to one or more trays,
    an automated tray handling system configured to receive the plurality of trays for larvae or the stack of trays for larvae and configured to move the plurality of trays or the stack of trays periodically to or from the feed distributer, wherein the automated tray handling system comprises a control unit and further comprises a support and drive system and a conveyance system,
        wherein the support and drive system comprises a ball transfer unit, a driven roller, a pneumatic arm and roller, a tray having wheels or casters, or a tray carrier having wheels or casters, and
        wherein the conveyance system comprises a hydraulic ram, a hydraulic plate, a conveyor, a telescopic piston, a carousel, a suction cup, or a robot.

7. A rearing module for rearing insect larvae, the module comprising:
    a transportable container, the transportable container comprising:
        a plurality of trays for larvae or a stack of trays for larvae,
        an automated tray handling system configured to receive the trays or the stack of trays at a loading/unloading point and configured to move the trays or the stack of trays periodically to or from the loading/unloading point, wherein the automated tray handling system comprises a control unit and further comprises a support and drive system and a conveyance system,
            wherein the support and drive system comprises a ball transfer unit, a driven roller, a pneumatic arm and roller, a tray having wheels or casters, or a tray carrier having wheels or casters, and
            wherein the conveyance system comprises a hydraulic ram, a hydraulic plate, a conveyor, a telescopic piston, a carousel, a suction cup, or a robot; and
        a feed distributer configured to deliver feed received from outside the transportable container to each tray repeatedly over a period of time, wherein the feed distributer comprises one or more arms for delivering feed, wherein each arm is configured such that a corresponding tray passes under the arm.

8. The rearing module of claim 7, further comprising:
    a heating, ventilation, and air conditioning system for controlling the temperature of the interior of the transportable container.

9. The rearing module of claim 7, wherein the automated tray handling system is configured to move the trays or the stack of trays around a closed path.

10. A method of operating a system for rearing insect larvae, the method comprising:
    providing:
        at least one container for a feed for insect larvae;
        at least one transportable container comprising:
            a plurality of trays for larvae or a stack of trays for larvae,
            a feed distributer configured to deliver feed to one or more trays,
            an automated tray handling system configured to receive the plurality of trays for larvae or the stack of trays for larvae and configured to move the plurality of trays or the stack of trays periodically to or from the feed distributer, wherein the automated tray handling system comprises a control unit and further comprises a support and drive system and a conveyance system, wherein the support and drive system comprises a ball transfer unit, a driven roller, a pneumatic arm and roller, a tray having wheels or casters, or a tray carrier having wheels or casters, and wherein the conveyance system comprises a hydraulic ram, a hydraulic plate, a conveyor, a telescopic piston, a carousel, a suction cup, or a robot; and a pump; and a tube running between the at least one feed container and the transportable container;

supplying feed for insect larvae, via the tube, from the least one feed container to the feed distributer of the at least one transportable container; and repeatedly moving the plurality of trays or stacks of trays to or from the feed distributer and delivering feed to the plurality of trays or the stacks of trays.

11. The method of claim 10, further comprising:
monitoring the transportable container; and
providing control signals to the transportable container.

12. The method of claim 10, wherein the trays or stacks of trays are moved around an internal perimeter of the transportable container.

13. The method of claim 10, further comprising harvesting the insect larvae.

14. The method of claim 13, further comprising feeding the harvested larvae to livestock.

\* \* \* \* \*